(12) United States Patent
Buechler et al.

(10) Patent No.: US 6,391,265 B1
(45) Date of Patent: *May 21, 2002

(54) DEVICES INCORPORATING FILTERS FOR FILTERING FLUID SAMPLES

(75) Inventors: Kenneth Francis Buechler, San Diego; Richard Roger Batt, San Jose, both of CA (US)

(73) Assignee: Biosite Diagnostics, Inc., San Diego, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/704,804

(22) Filed: Aug. 26, 1996

(51) Int. Cl.[7] ............................................... G01N 33/48
(52) U.S. Cl. ........................ 422/101; 422/61; 210/496; 210/506
(58) Field of Search ........................... 422/101, 58, 61; 436/169, 170, 177; 210/435, 446, 496, 505, 506, 508, 509

(56) References Cited

U.S. PATENT DOCUMENTS

| | | | | |
|---|---|---|---|---|
| 5,087,556 A | * | 2/1992 | Ertinghausen | 422/58 |
| 5,139,685 A | * | 8/1992 | De Castro et al. | 436/170 |
| 5,516,488 A | * | 5/1996 | Bunce et al. | 422/58 |
| 5,916,521 A | * | 6/1999 | Bunce et al. | 422/58 |
| 5,989,921 A | * | 11/1999 | Charlton et al. | 411/58 |

* cited by examiner

*Primary Examiner*—Lyle A. Alexander
(74) *Attorney, Agent, or Firm*—Foley & Lardner

(57) ABSTRACT

Devices and use thereof, the device comprising a filter and a means for region specific compression of the filter. Alternatively, a single step assay device whereby fluid movement through the device occurs substantially solely due to action of capillary force, the device comprising a filter; a region containing the filter; a fluid access port to the region containing the filter; a means for retarding movement of particles through a peripheral filter surface; a fluid egress port from the region containing the filter; a lateral fluid flow path through the filter connecting the fluid access port to the fluid egress port, whereby sample fluid substantially devoid of particulate matter is released from the filter through the egress port; and, an exit region fluidly connected to the egress port.

18 Claims, 6 Drawing Sheets

DEVICES INCORPORATING FILTERS FOR FILTERING FLUID SAMPLES

FIELD OF THE INVENTION

This invention relates to devices comprising filters for filtering fluid samples. In a particular embodiment, the filter-containing devices filter cells or particulate matter from biological samples and introduce the filtrate into a capillary space, and operate without the use of any externally applied force.

BACKGROUND ART

With the advent of point of care testing in hospital emergency departments, it has become increasingly important to develop diagnostic products which are simple, rapid and convenient for the user to perform. This need has arisen because health care workers in an emergency department need results rapidly with a minimum of time given to the performance of a diagnostic test. Providing a diagnostic result in minutes allows a physician to treat a patient as soon as possible.

Point of care diagnostic tests frequently are performed on biological samples, such as whole blood or urine. Cells and particulate matter in biological samples can interfere with fluid flow in a test device, and thus impair the measurement of analytes in the biological fluid.

For example, in blood, red blood cells can interfere with spectroscopic measurements, and as the hematocrit varies, the volume of plasma in a given volume of blood varies. To overcome these problems, red blood cells are separated from plasma to allow for a more defined and uniform sample.

As a further example, urine can contain lymphocytes that can affect spectroscopic measurements, and flow through filters and capillaries. Thus, a device to filter out cells, particulate matter, or debris from a biological sample can improve the quality of an analytical procedure performed on the sample.

To achieve removal of particulates, incorporation of a filter into an assay device has been described in the prior art. For example, U.S. Pat. Nos. 4,477,575; 4,753,776; 4,987,085; and 5,135,719 refer to blood filter devices whereby a transverse flow of blood through a filter results in the separation of red blood cells from plasma. Sealing of the filter in the device to achieve effective filtration, and not allow sample to bypass the filter, has been a problem in the prior art. A small capillary or gap between the filter and the filter chamber walls often existed due to poor initial sealing, or because the gap formed with time. As a consequence, particulates in a fluid sample travel in the capillary space or gap rather than through the filter. Particulate matter which travels around the filter decreases the filtration efficiency, repeatability, and may cause the filter to be unacceptable for certain applications. Techniques, such as using glues, tapes and the like have been used to seal a filter into the filter chamber of such devices. The use of these materials to affect sealing has produced variable, and often poor sealing. Additionally, these sealing methods resulted in absorption of variable amounts of the sealing compound into the filter.

Another drawback of prior art filter devices is consequent to use of a relatively short transverse fluid flow path through a filter. The transverse flow path in a conventionally shaped filter (a filter with a length, width and substantially thinner depth) is the distance between the top and the bottom of the filter, the filter depth commonly referred to as the filter thickness. Filters are generally 0.1 mm to 6 mm thick, this relatively short flow path produces relatively poor separation efficiency. A longer flow path would allow more particulates to be removed from fluid, thus, increasing the separation efficiency. U.S. Pat. Nos. 4,678,757; 5,135,719; 5,262,067 and 5,435,970, comprise filters treated with materials such as carbohydrates, agglutins and lectins, to affect separation of red blood cells from plasma. However, due to the relatively short fluid flow path, the filtration efficiencies in these teachings are not optimal. European Appl. No. 89300416.8, describes methods and devices which bind red blood cells to treated polycationic filters. However, treatment of filters introduces an additional process in device fabrication. A filter-device design that does not require treatment would be advantageous since the filter would be too costly and device manufacture would be less complicated; less complicated device designs are easier and more cost-effective to manufacture.

Embodiments with longer transverse flow paths have also been disadvantageous, however. U.S. Pat. No. 5,139,685 ("the '685 patent"), describes a cylinder of stacked filters, so that the device has a relatively long flow path. Although the '685 patent has a relatively long transverse fluid flow path pursuant to stacking of discrete filters, applications of this technique are limited. Namely, in the '685 patent, discrete filters are stacked and are under an applied pressure to achieve an efficient filtration of red blood cells from plasma. The pressurization of the filters is necessary to achieve a fast and efficient separation of particulate matter from the sample.

The relatively large amount of space required and the configuration of a design of the '685 patent does not lend itself to a convenient point of care diagnostic testing. Point of care diagnostic testing is facilitated by smaller and more convenient designs that can be easily manipulated by a health care worker, designs which are capable of being fed into hand-held instruments that provide quantitation of assay results. Devices capable of being fed into hand-held instruments (such as a reader) should be small and flat, and have smooth surfaces. Preferably a point of care device would not require an externally applied pressure.

Thus, there is a need for an efficient, compact, costeffective filtration device. There is also a need for a means to effectively seal a filter within a device, whereby the fluid flow path is optimized, leading to increased filtration efficiency. Most desirably, there is a need for a sealing means that makes device fabrication tolerances less crucial and device manufacture more economical.

DESCRIPTION OF FIGURES

FIGS. 1A, 1B, 1C, and 1D show one embodiment of a device in which

FIGS. 2A, 2B, and 2C show another embodiment of a device in which

FIGS. 3A, 3B, and 3C show another embodiment of a device in which

FIGS. 4A, 4B, 4C, 4D and 4E show another embodiment of a device in which

FIGS. 5A, 5B, and 5C show another embodiment of a device in which

FIGS. 6A, 6B, 6C and 6D show another embodiment of a device in which

DISCLOSURE OF THE INVENTION

The present invention provides for simple and rapid filtering of biological samples, whereby a sample can be analyzed in the same device or a different device.

In one embodiment, the present disclosure teaches the use of lateral flow through filters and the use of capillary force to cause the exit of filtrate fluid from filters and into a capillary space.

Alternative embodiments of a device of the invention comprise are where the device comprises a filter and a means for region specific compression of the filter. Alteratively, the device comprises a filter; a region containing the filter; a fluid access port to the region containing the filter; a fluid egress port from the region containing the filter; and a lateral fluid flow path through the filter connecting the fluid access port to the fluid egress port. Alternatively, a single step assay device whereby fluid movement through the device occurs substantially solely due to action of capillary force, the device comprising a filter; a region containing the filter; a fluid access port to the region containing the filter; a means for retarding movement of particles through a peripheral filter surface; a fluid egress port from the region containing the filter; a lateral fluid flow path through the filter connecting the fluid access port to the fluid egress port, whereby sample fluid substantially devoid of particulate matter is released from the filter through the egress port; and, an exit region fluidly connected to the egress port. Use of the device optionally comprises means for a producing an assay result in an exit region of the device.

LIST OF REFERENCE NUMERALS

10 Base
12 Filter Cavity
14 Fluid Access Port
15 Fluid Access Region of Filter 20
16 Fluid Egress Region of Filter 20
17 Exit Region
18 Lid
20 Filter/Filter Matrix/Membrane
22 Compression Structure
23 Support Bar
24 Dead Space of Filter Cavity 12
26 Sample Reservoir
28 Filter Supports/Posts
30 Vent Holes
32 Filter Stays
34 Grooves
36 Lateral Compression Region of Compression Structure 22
38 Proximal Compression Region of Compression Structure 22
40 Distal Compression Region of Compression Structure 22
42 Lid Cavity

MODES FOR CARRYING OUT INVENTION

This invention describes novel devices comprising filters for the rapid filtering of samples, particularly chemical, environmental, or biological samples, and preferably for introduction of the filtered sample into a capillary space. This invention can be utilized in any device format in accordance with the teachings provided herein. For example, although assay device filters of conventional configuration are discussed, it is understood that the principles of the application apply to devices with other configurations. In a preferred embodiment, the invention is used with the technology of devices described in U.S. Pat. No. 5,458,852 to Buechler, incorporated herein by reference. Aspects of the invention are discussed below.

Lateral and Transverse Fluid Flow

As used herein, fluid flow will be described as follows: a conventional filter has a width, length, dimensions and substantially smaller depth ("thickness") dimension. For a filter with such dimensions, transverse flow is perpendicular to the length and width of the filter, and is predominantly in a direction parallel to the depth of the filter. Conversely, lateral flow is predominantly parallel to the length or width planes of a filter. Alternatively, a lateral flow path is a distance greater than a transverse flow path distance through a filter, typically these flow paths are oriented perpendicular to each other. In one embodiment of the invention, a lateral fluid flow path is through a filter connecting a fluid access port to a fluid egress port, where the flow path is greater than or equal to that of the greatest cross sectional distance of the filter as determined perpendicular to any point along the flow path.

Conventional device filters comprise some degree of capillarity. To a certain extent, fluid moves through the filter due to capillary forces created, e.g., by small diameter pores or the close proximity of fibers. Fluid may move through such a filter with or without external pressure. On a micro scale relative to the filter's overall dimensions, fluid travels in multiple directions as a result of capillary forces. On a macro scale, however, fluid travels in one direction; i.e., through the filter in a predominantly lateral or transverse direction to a location where fluid can exit the filter.

To filter a sample, either lateral or transverse fluid flow requires at least one fluid input surface and at least one fluid egress surface. A fluid input surface is defined as the filter surface where unfiltered sample fluid is placed in contact with the filter; the fluid egress surface is a filter surface from which the majority of a filtered sample fluid ("filtrate" or "filtration liquid") exits. As discussed below, a smaller amount of fluid can exit from peripheral surfaces in certain embodiments. A peripheral surface is defined as being a surface that is not a fluid input surface and not a fluid egress surface. For transverse flow, the input and egress surfaces are the top and bottom surfaces of a conventionally shaped filter, e.g.,.surfaces parallel to the length and width planes. Alternatively, for a filter having lateral fluid flow, input surfaces and egress surfaces can be on the top, bottom or any surface which is not a peripheral filter surface.

In accordance with the present disclosure, a preferred flow directionality through a device filter is lateral flow. Compared to transverse flow, lateral flow has several advantages. First, the fluid flow path can be dramatically increased in a filter of a standard configuration. For a filter of conventional shape, lateral flow yields greater filtration efficiency than transverse flow since the lateral fluid flow path is longer than the transverse fluid flow path. For example, conventional assay filters generally have a thickness of between 0.1 mm and 6 mm, approximately 2 mm is most common, with a length and width substantially longer than the thickness usually on the order of several centimeters. Thus, lateral flow yielded greater filtration efficiency with minimum effects on the device's shape. Second, lateral flow within a filter allowed the addition of fluid to any region of the filter that is not a fluid egress region, so long as fluid could laterally flow through the filter to the fluid egress region thereof. In lateral flow devices, addition of fluid to regions of the filter which are not fluid egress regions allowed fluid to enter the filter at an effectively larger area (approx. 2 times) than by entering only on one side. The larger area for fluid entrance provided a more efficient use of the filter, maximizing flow rate through the filter and minimizing the potential for clogging with particulate matter which is to be filtered from a sample.

Additionally, incorporating a single filter rather than a stack of several filters in a device conserves device space and permits the filter to be easily situated on a device, allowing a plethora of possible design configurations.

Filter Materials

Various filter materials are available for filtering cells and particulate matter from biological samples. For example, cellulose fibers, nylon, glass fibers, polyester fibers or combinations of these materials are useful to make filters that remove debris from samples, e.g., cells from urine and red blood cells from plasma.

The filter is preferably chosen such that the pores or fibrous matrix of the filter do not get clogged by particulate matter from the sample. In the case of separating red blood cells from plasma, filters generally bind, retain or retard the red blood cells and allow plasma to separate from blood and pass through the filter.

Filters can comprise a fibrous matrix or porous material. A preferred filter is a fibrous matrix filter that is made of borosilicate glass microfibers. Borosilicate glass microfiber filters permit filtration of whole blood samples by permitting the sample (including particulate matter such as red blood cells) to penetrate the filter. For whole blood samples, the filter retards red blood cells and allows plasma to move through the fiber matrix at an nonretarded, higher flow rate. When these filters were used, and cells and plasma moved through the filter, the plasma moved further ahead of the red blood cells.

Alternative filters can also be used which have a more porous structure, for example filters comprising nitrocellulose, acrylic copolymers, or polyethersulfone. These filters, generally, functioned differently than filters comprising fiber matrices, in view of the fact that they have pore-like passages typically of uniform diameters. Typically, a porous filter is selected such that the pore diameters are smaller than the diameters of the particulates desired to be separated from a sample. These filters retain rather than retard the red blood cells, i.e., red cells generally do not penetrate the filter beyond its surface. One skilled in the art will recognize that if the particulate matter in a sample is approximately the same size or greater than the pores of a filter, the particulate matter will rapidly clog the pores and slow or stop fluid flow therethrough.

Thus, in accordance with the present disclosure, various filters can be used. A filter may be one of several commercially available filters including but not limited to Ahlstrom CytoSep (Mt. Holly Springs, PA) or Micro Filtration System's (Dublin, CA) glass fiber media. U.S. Pat. Nos. 5,186,843; 4,774,039; 4,629,563, and 5,171,445, cover the compositions of these and like media.

Sample Reservoir

Preferably, a sample reservoir accomplishes several functions: 1) it delimits a volume which is sufficient to achieve an assay result, and thus facilitates a device user's ability to provide the suitable volume; 2) it accomplishes the foregoing while allowing for a diverse range of input volumes in a manner which does not impair an assay result; and, 3) a reservoir that is a capillary space helps to prevent fluid escape. In a preferred embodiment, the sample reservoir contained a fluid volume approximately 100 times the volume needed for downstream processing of a sample.

Figure 6A:
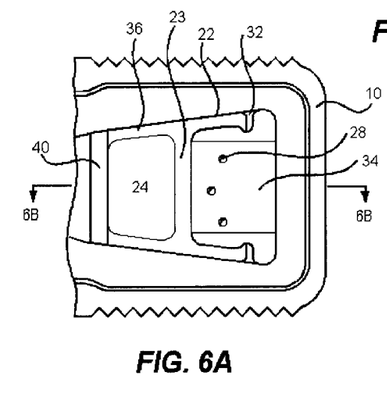
FIG. 6A is a top view of base 10.
Figure 6B:
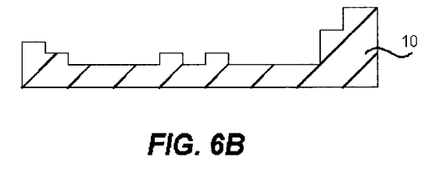
FIG. 6B is a cross-section of base 10, viewed along plane 6B—6B of FIG. 6A.
Figure 6C:
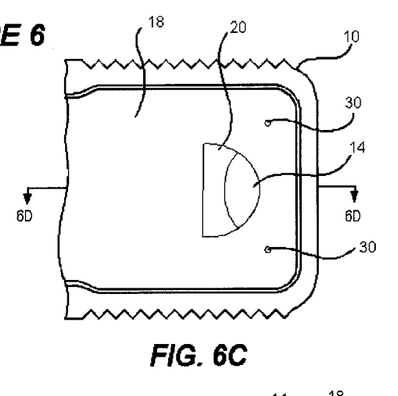
FIG. 6C is a top view of an assembled device of this embodiment.
Figure 6D:
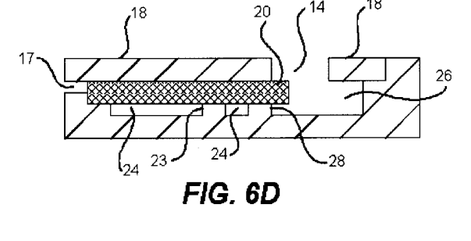
FIG. 6D is a cross section, viewed along the plane as 6D—6D of FIG. 6C, of an assembled device including a filter 20, lid 18, and base 10.

As depicted in FIGS. 6A, 6B, 6C and 6D, a sample reservoir 26 comprising a capillary space is incorporated into the device, whereby sample was contained in the capillary space of the sample reservoir, and the reservoir was in fluid communication with an edge, top and/or bottom of the filter (FIG. 6D). An advantage of utilizing a capillary space for introducing the sample to the filter is that the fluid, for example, a hazardous chemical, environmental or biological fluid, contained in a capillary space will tend not to spill or leak from the device.

"Sealing" of Peripheral Surfaces of a Filter

Preferably the peripheral surfaces of the filter are sealed within the device: 1) so that fluid must flow through the filter; and 2) to prevent the fluid sample, e.g., particulates, from flowing around the filter in a capillary between the filter and the device, thus contaminating the filtrate. Sample that travels around the filter in a capillary space, rather than through the filter, can enter the exit region 17. When unfiltered fluid enters exit region 17, the filtering efficiency of the device is decreased. "Sealing" of the peripheral surfaces need not be liquid-tight, sealing in accordance with the invention also comprises the ability to retard to flow of liquid and particulates, or particulates into spaces between the filter and the walls of the device adjacent to the filter.

There are several methods to achieve sealing of the peripheral surfaces of a filter. Preferably the sealing is liquid-tight, although some liquid release is acceptable so long as a low resistance fluid flow path outside the filter does not result. In one embodiment, the sealing permits liquid between the device wall and the filter, but retards the development of a capillary space along the peripheral surfaces and the sealing also may serve to retain particulate matter in the filter and not in any space along peripheral surfaces, due to compression. In any event, there is preferably particle-tight, more preferably liquid-tight and most preferably fluid-tight sealing of the device at or near the fluid access region 15 of filter 20.

Regardless of the flow path direction, filter surfaces may be sealed using one or a combination of the following techniques: pressure-adhesive tapes, glues, or sealants. Such techniques require careful placement of the sealant along edges of the filter and the side walls of filter cavity 12. A preferred liquid sealing of the peripheral surfaces is achieved by a pressure fit. A pressure fit may be achieved by placing a slightly oversized filter into filter cavity 12 such that all the peripheral surfaces of the filter are in contact with the walls of the filter cavity. Concerning length and width dimensions, a filter is preferably 1–10% and more preferably 1 to 5% larger than the filter cavity into which it is to be placed to ensure direct contact. Compression of the depth dimension is discussed in greater detail below. Direct contact between the filter and the filter cavity walls discourages fluid from traveling between the peripheral surfaces of the filter and the filter cavity walls, because a capillary space does exist between the filter and the device walls. Thus, the perimeter or side edges of the filter will maintain contact with the walls of the filter cavity 12 as depicted in FIG. 1A.

The filter must have a degree of resilience such that it may be squeezed and hold its shape over time. The conventional media described herein have these properties and can be employed as disclosed herein to effectively seal particulates and/or liquid. The more pliable a filter is, the larger the filter must be relative to the cavity into which it is placed, so as to assure that the filter provides pressure against the cavity walls and a low resistance fluid flow path is avoided.

Figure 1A:
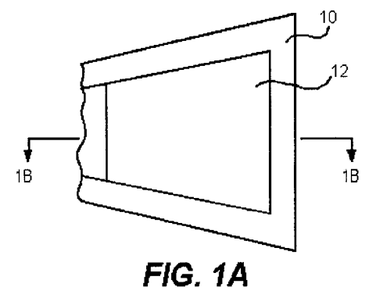
FIG. 1A is a top view of base 10.
Figure 1B:
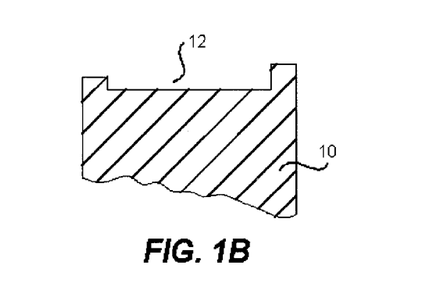
FIG. 1B is a cross-section of base 10.
Figure 1C:
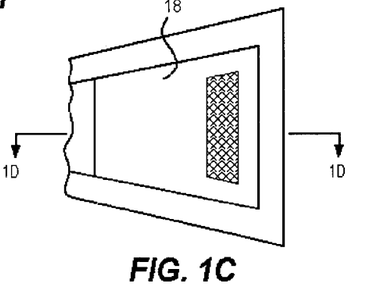
FIG. 1C is a top view of an assembled device taken along plane 1B—1B in FIG. 1A.

To prepare a device in accordance with the invention, the shape of the filter must be approximately identical to the filter cavity, 12,(FIG. 1A). Filter cavity 12 may be of any three dimensional shape, e.g., trapezoidal, rectangular, rounded or the like. A presently preferred filter shape is that of the filter cavity 12 of FIGS. 1A–1D.

Region Specific Compression of the Filter

Preferred embodiments of the invention make use of compression of the filter in distinct areas to limit or retard the movement of particulate matter (e.g., cells or debris) within the filter and to prevent particulate matter from escaping the filter and traveling along the peripheral filter surfaces. In the case of preventing fluid from flowing along peripheral surfaces of the filter, a compression structure 22 (e.g., see FIGS. 2, 3, 4 or 5A) in filter cavity 12 helps to prevent the formation of capillary gaps between the filter 20 and a surface to which it is in contact, e.g., lid 18 or a surface defining cavity 12. Capillary gaps are to be avoided as they provide a low resistance flow path to fluid exit region 17, and thereby permit unfiltered sample to contaminate the filtrate.

In addition to region specific compression, liquid sealing of the filter peripheral surfaces by use of capillary force, glues, pressure-sensitive tapes, or sealants can be used to prevent particulate escape and flow of liquid along the peripheral surfaces. It is advantageous to avoid glues, pressure sensitive tapes or sealants since they have a tendency to lose their sealing properties with time; and the sealant in such materials tends to leach through the filters, potentially affecting the filtrate. In contrast, region specific filter compression leads to a lasting seal and functions without any additives or additional parts; thus, it decreases the complexity of the fabrication process and avoids potential contamination of the filtrate.

Structures using region specific compression are shown, for example, in the embodiment depicted in FIG. 4. Referring to the top view FIG. 4A, a compression structure 22 is shown. Preferred degrees of compression of the thickness of filter 20 by compression structure 22 and an abutting surface such as lid 18, are 1 to 50% and more preferably 1 to 30% of the native thickness of the filter. Accordingly, in preferred embodiments of the device only specific regions of a filter are compressed; all regions of the filter are not compressed, and flow rate is not unduly impeded. Thus, one advantage of the present invention is that effective and rapid filtration is achieved.

Figure 4A:
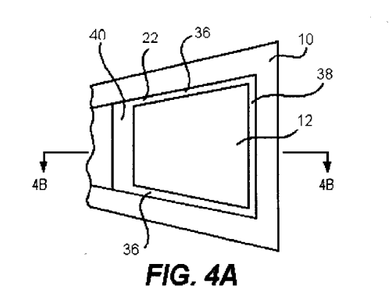
FIG. 4A is a top view of base 10.
Figure 4B:
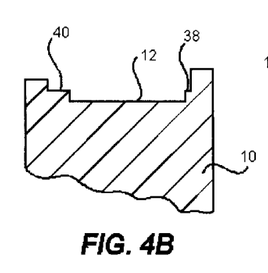
FIG. 4B is a cross-section of base 10 viewed along the plane 4B—4B of FIG. 4A.
Figure 4C:
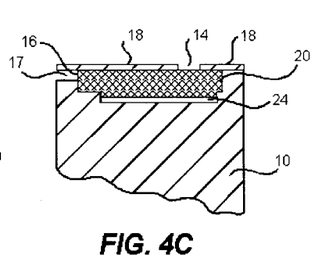
FIG. 4C is a cross section, along the same plane as FIG. 4B, of an assembled device including a filter 20, lid 18, and base 10.

The cross section view of an assemble device in FIG. 4C displays a preferred height change between filter cavity 12, and compression structure 22. This height change results in dead space 24 (e.g., in FIG. 4C) underneath filter 20 upon placement of filter 20 in cavity 12.

Dead space 24 effectively leads to liquid sealing, since dead space 24 has minimal capillary force, and therefore does not draw any fluid away from or out of filter 20. The capillary force is low for dead space 24 due to a relatively large gap between filter 20 and filter cavity 12.

Region specific compression leads to liquid sealing yet also facilitates rapid fluid flow through the filter. The filter region depicted above the dead space is not compressed to the same degree as the filter regions between compression structure 22 and an abutting surface. The pores or matrices of the filter are not appreciably compressed in this area and fluid flow therethrough is facilitated. It is advantageous to keep the filter noncompressed in embodiments where maximum flow rate from the fluid egress region is desired.

In summary, dead space 24 results from certain compression structure designs and is useful for several reasons. First, it has minimal capillary force and draws no fluid into its cavity. Thus, a liquid seal is formed along the respective filter surface adjacent the dead space, forcing fluid to flow through the filter. Second, the filter adjacent to the dead space is not compressed and therefore the pore or fiber structure within the filter remains unchanged; such filter configuration is in contrast to the prior art, and advantageously produces higher flow rates.

Figures 5, 5A:
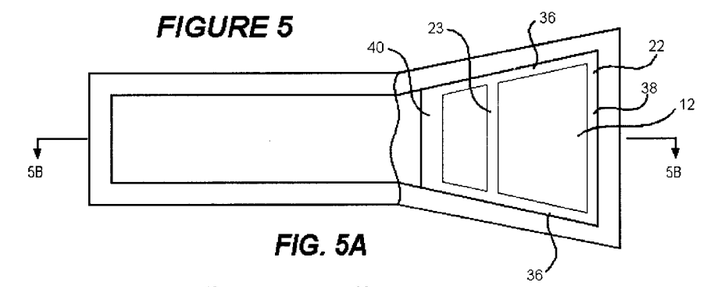
FIG. 5A is a top view of base 10.

As noted, preferred degrees of compression of filter 20 by compression structure 22 and lid 18 are 1 to 50%, preferably 1 to 30% of the native thickness of the filter. To achieve such compression, compression structure 22 need not be limited to one uniform level or height. Rather, compression structure 22 may be comprised of multiple sections at the same or different heights. FIG. 5A displays an embodiment of the present invention in which compression structure 22 is comprised of sub-regions including: support bar 23, lateral compression regions 36, proximal compression region 38, distal compression region 40. Each sub-region may be sized to yield compression that facilitates sealing, filtration, or flow rate properties. In the embodiment of FIG. 5, the combination of support bar 23, lateral compression regions 36, and distal compression region 38 force filter 20 to be in contact with lid 18 forming a preferably liquid tight seal above each sub-region, thus facilitating prevention of flow along the peripheral surfaces of the filter. Distal region 40 does not form a liquid-tight seal, but permits liquid to exit at fluid egress region 16. Accordingly, filter 20 is not uniformly compressed, but rather is compressed only above the subregions of compression structure 22.

Another advantageous aspect of region specific compression is the ability to retard particulate matter from designated regions of the filter. Namely, to retard particulate matter from reaching either the peripheral edges or the fluid egress region of a filter. Retardation of particulate movement occurs since compression of a filter causes concomitant compression of the fiber spacing and/or pores in the filter; the compression of these microstructures makes it more difficult or impossible for particulate matter or cells to travel therethrough.

One skilled in the art will recognize that the selective compression of the filter at the compression structure 22 is not required for the separation of the particulate matter from the sample, but rather, such compression is but one embodiment than can be utilized for sealing the peripheral surfaces of the filter in a device and for modulating particulate movement. In a preferred embodiment, no particulate matter can exit along the peripheral surfaces or the fluid egress region of filter 20. In an alternative embodiment employing compression structure 22, particulate matter is retarded in its movement through the filter, but nevertheless is capable of exiting the filter; in this embodiment, the exit region preferably holds the amount of liquid that is required to produce an assay (via a material(s) or modality(s) for achieving an assay result appreciated by those of skill in the art), where that volume is less than the volume of fluid that flows through he filter ahead of the retarded particulate matter.

Exit Region in Fluid Communication with Fluid Egress Region of Filter

Figure 1D:
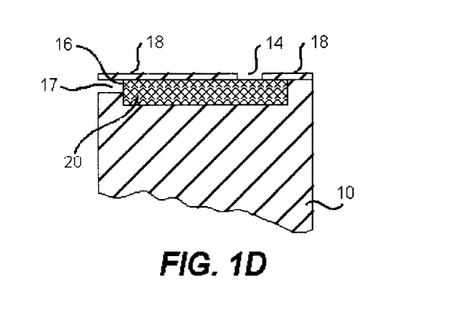
FIG. 1D is a cross section of an assembled device including a filter 20, lid 18, and base 10 taken along plane 1D—1D in FIG. 1C.

In a preferred embodiment, after the particulate-free fluid has passed through the filter it is preferably drawn into a fluid exit region 17 (see, e.g., FIG. 1D). Preferably, exit region 17 comprises higher capillarity than filter 20 to facilitate fluid flow therebetween. Thus, a preferred embodiment of the invention utilizes capillarity force, whereby fluid egress area 16 of the filter is immediately adjacent to exit region 17, and region 17 is a capillary space. Due to the use of capillarity as taught herein, fluid leaves the filter without an external pressure and uniformly fills the capillary space of exit region 17, and fluid will not enter any region with lower capillarity than the filter, e.g., dead space 24. Thus, capillary force can be used to cause egress of fluid from the filter and into an exit region 17 without the application of an external pressure such as hydrostatic pressure. In accordance with this embodiment, compression of the filter by compression structure 22, in particular distal compression region 40, should not cause the pores of the filter to be made sufficiently small such that the capillary force holding the fluid within the filter is greater than the capillarity of exit region 17.

Device Assembly

Advantageously, devices that incorporate filters that function by lateral flow, can be designed so that the overall device thickness is not constrained by the filter thickness.

The filtration devices described herein generally require assembly and joining of several parts. Lid 18 and base 10 can be fabricated from conventional materials compatible with chemical, environmental or biological fluids to be assayed, for example: a plastic material such as acrylic, polystyrene, polycarbonate, or like polymeric materials; as well as silicon composites, such as silicon semiconductor chips; glass; or metal. In the case of plastic polymeric materials, lid 18 and base 10 may be fabricated using thermal injection molding technology or machining. In the case of fabricating the lid and base from silicon composites, micromachining and photolithographic techniques, commonly used in the field of electronics, can be utilized to create chambers and capillaries.

The base 10 and lid 18 are contacted together in order to form the physical configuration desired to achieve a particular result. Ultrasonic welding, adhesives, physical interfitting and heat welding are some of the methods that may be used to join base 10 and lid 18. For example, with embodiments comprising a lid of silicon composite or plastic, and a base of plastic or silicon composite, the base and lid can be joined with adhesives.

In a preferred embodiment, the plastic surfaces of base 10, lid 18, or both are made hydrophilic or "wettable", whereby the contact angle between the sample fluid meniscus and the base 10 and lid 18 is decreased. There are several ways to decrease the contact angle including but not limited to corona discharge, plasma treatment or the drying down of various surfactants or proteins onto surfaces. In accordance with standard methodologies, exposing a plastic surface to a corona discharge or plasma gas results in the formation of functional groups on the surface. The surface chemistry as well as the degree of hydrophobicity are thus modified and can be used for a variety of applications. For example, time gates, as described in U.S. Pat. No. 5,458,852 to Buechler (entirely incorporated by reference herein), can be incorporated at the fluid egress region to provide an incubation time for the sample within the filter.

EXAMPLES

One skilled in the art will recognize, in view of the present disclosure, that the filter cavity can have many possible design configurations or embodiments. The filtration concepts disclosed herein can be incorporated into a variety of devices that can be used in various assays. The following examples demonstrate presently preferred embodiments and are not intended to limit the invention.

Example One

An embodiment of the present invention is shown in FIG. 1. Base 10 was fabricated using injection molding technology and was made of white acrylic copolymer (Polysar NAS® 30, Polysar, Inc., Madison, CT). The overall device length, width and thickness were 8.7, 3.5 and 0.26 cm respectively. The surface of base 10 was made hydrophilic by a corona discharge treatment.

In accordance with standard methodologies, filter cavity 12 (FIGS. 1A, 1B) was formed into base 10. The filter cavity had a bilaterally symmetrical trapezoidal shape, with parallel sides 1.0 and 1.34 cm long and 0.72 cm apart. A filter 20, slightly oversized 1–30% preferably 1–5% relative to filter cavity 12, was fitted into the cavity (FIG. 1D). The filter (# GB100R, Micro Filtration Systems ("MFS"), Dublin, CA) consisted of borosilicate glass fibers; its thickness was 0.038 cm and had an absorption volume of approximately 50 µl.

A clear plastic lid 18 (FIG. 1C, 1D) was coupled to base 10 by ultrasonically welding using a Branson 941 AE welder (Branson Inc., Danbury CT) set at 50 joules and 40 psi. Bonding lid 18 to base 10 slightly compressed the filter 20. This compression created a seal that served to prevent fluid and particle flow around the peripheral edges of filter 20. Referring now to FIG. 1D, fluid access port 14 was located directly over the filter. Lid 18 and base 10 formed a capillary space in exit region 17 adjacent to fluid egress region 16 of filter 20. Despite the increase in capillarity by compressing filter 20, exit region 17 comprised sufficient capillarity to draw filtrate fluid, e.g. plasma, out of filter 20. In this embodiment the exit region comprised a capillary space, where a cross section of exit region 17 immediately abutting fluid egress region of filter 20 had dimensions approximately 25 μm by 1.0 cm. The volume encompassed by this exit region is preferably a volume sufficient to permit enough fluid to flow through the device so that an effective assay result is obtained (via a material or modality appreciated by one of ordinary skill in the art), after which the exit region is filled with fluid and flow stops; for such an embodiment an escape port is present (not illustrated) that permits release of gaseous fluids but not liquid fluids.

A use of the embodiment depicted in FIG. 1 was as follows: fresh human whole blood (70 μl), that was drawn in a Vacutainer® Blood Collection Tube with acid citrate dextrose (ACD), was added to fluid access port 14. Some of the blood was immediately absorbed into filter 20 and the remainder formed a small droplet covering fluid access port 14. As the fluid moved by lateral flow through filter 20, two distinct flow fronts formed. Since the filter retarded flow of particulates, the two flow fronts consisted of a clear plasma front preceding a dark front of red blood cells. Thus, the plasma front reached egress region 16 of the filter before the red cells, and particulate depleted filtrate entered exit region 17 before the red blood cell flow front reached the end of the filter.

Example Two

Figure 2A:
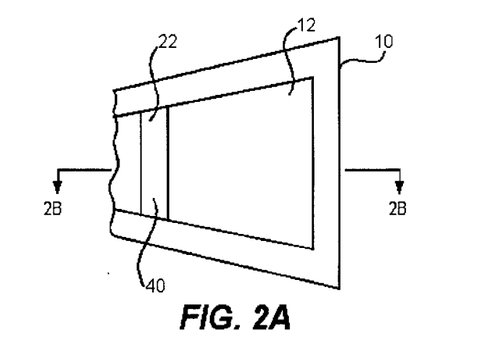
FIG. 2A is a top view of base 10.
Figure 2B:
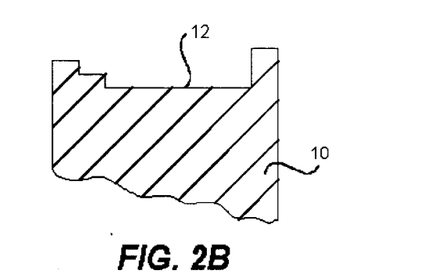
FIG. 2B is a cross-section of base 10 taken along plane 2B—2B in FIG. 2A.

Another embodiment of this invention is depicted in FIG. 2. Base 10 is fabricated using injection molding technology and is made of white acrylic copolymer (Polysar NAS® 30, Polysar, Inc., Madison, CT). The overall device length, width and thickness were 8.7, 3.5 and 0.26 cm respectively. The surface of base 10 was made hydrophilic by a corona discharge treatment.

Figure 2C:
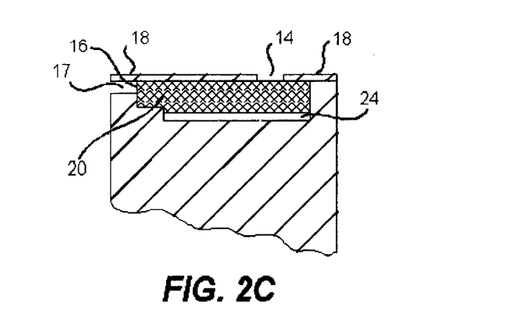
FIG. 2C is a cross section taken along the cross-sectional plane in FIG. 2B of an assembled device including a filter 20, lid 18, and base 10.

Base 10 comprising compression structure 22 was formed by conventional methods. A slightly oversized filter 20(FIG. 2C) was fitted over compression region 22 causing dead space 24 to be defined (FIG. 2C). The filter was 1–30%, preferably 1–5% larger than the portion of the filter cavity 12 which did not include the dead spare 24. The filter (MFS filter, cat. no. GB100R Micro Filtration Systems, Dublin, CA) consisted of borosilicate glass fibers. Its thickness was 0.038 cm and had an absorption volume of approximately 50 μl. Thus, there was sealing between fluid access port 14 and fluid access region 15 of filter 20, so that essentially the only way sample could enter the filter was through region 15.

Advantageously, this embodiment comprises dead space 24 (FIG. 2C). In prior art devices, fluid could accumulate in a capillary space between the filter and device walls around the filter. The formation of fluid in the capillary space is believed to result from a relatively high capillary force created by the close contact of the filter with the filter cavity and by the deformability of the filter. Fluid formation in such regions is undesirable since it can provide a route whereby sample does flow entirely within the filter, and if particulates enter the space separation efficiency is decreased. The present invention decreases potential fluid formation between filter 20 and a wall of cavity 12 by means of a space (dead space 24) that has virtually no capillary force. Therefore, so long as capillary force is used to move fluid through the filter fluid exits only from the designated region, namely, fluid egress region 16.

A clear plastic lid 18 (FIG. 2C) was coupled to the base by ultrasonic welding using a Branson 941 AE welder set at 50 joules and 40 psi. Bonding of lid 18 to base 10 slightly compressed filter 20 above compression structure 22: the filter was compressed by 1–50%, preferably 1–30% relative to its native thickness. This region specific compression created a sufficient seal to serve to prevent fluid flow over the peripheral surfaces of the filter at that region and to retard particles within the filter compressed at that region. Fluid access port 14 was located directly over the trapezoid-shaped filter. As shown in FIG. 2C, lid 18 and base 10 defined a fluid egress region from the filter 16 adjacent to the downstream edge of filter 20. A cross section of exit region 17 immediately adjacent fluid egress region 16 had dimensions approximately 25 μm by 1.0 cm.

For the embodiment depicted in FIG. 2, a thin film lamination may be applied to the filter to increase the filter's rigidity, to avoid having the filter fall into dead space 24 when sample is added. The lamination also prevents bending of the filter in a region where the filter is unsupported; bending can lead to flow of fluid and particulates along a peripheral surface causing contamination of the filtrate, and is generally to be avoided. Pressure sensitive tape such as ARcare ®7396 (Adhesives Research, Inc., Glen Rock, PA) is one example of a commercially available plastic lamination film which has been used.

The embodiment of FIG. 2 was used as follows: Fresh human whole blood (70 μl), was drawn in a Vacutainer® Blood Collection Tube with ACD, and was added to fluid access port 14. Some of the fluid was immediately absorbed into filter 20, and the remainder formed a small droplet covering fluid access port 14. Due to the retarding of particulate flow through the filter, as the fluid laterally moved through filter 20, two distinct flow fronts formed. The two flow fronts consisted of a clear plasma front preceding a dark front of particulate matter comprising red blood cells. Thus, the plasma front reached the downstream edge of filter 20 before the red cells, and by the time particulate matter reached the downstream edge, clear plasma had already entered exit capillary 17. Exit capillary 17 contained material(s)/modality(s) for conducting an assay on the filtrate fluid, e.g., plasma, thus an assay was performed substantially without contamination from particulate matter, e.g., red blood cells.

In general, fluid continues to flow from filter egress region 16 into exit region 17 until the fluid sample at access port 14 is depleted into the device or until the volume that exit region 17 can contain is filled. With this concept in mind, an embodiment of a device of the invention was designed to hold a specific volume of filtrate (e.g., plasma) in exit region 17, for example, as in devices described in U.S. Pat. No. 5,458,852 to Buechler; once the exit region contained the specified volume of liquid, fluid flow through the device stopped. The fluid flow stopped whether or not sample remained at the access port 14 or sample reservoir 26; thus, the addition of too much sample had no negative affect on device function.

As depicted in Table 1, use of the embodiment of Example 2 yielded a flow rate of plasma out of filter 20 of up to 8 μl/min. Use of this embodiment provided recovery of at least 6 μl of plasma. The effect of varying the area of filter compression at the distal compression region 40 is shown in Table 1. As the area of the distal compression region 40 was decreased from 0.041 $in^2$ to 0.004 $in^2$, the percent area of compression of the filter 20 concomitantly decreased from 32% to 3%, and the flow rate of plasma through the filter increased from 1 μl/min to 8 μl/min at a constant filter compression of 40%. This data showed that the flow rate of fluid from the filter can be controlled by the area of the filter that is compressed.

TABLE 1

EFFECT ON FLOW RATE BY VARIATIONS OF FILTER
AREA COMPRESSED AT DISTAL REGION 40
(40% FILTER THICKNESS COMPRESSION)

| AREA[1] | % AREA COMP[2] | FLOW RATE $\mu$l/MIN |
|---|---|---|
| 0.041 | 32 | 1 |
| 0.028 | 22 | 2 |
| 0.014 | 11 | 4 |
| 0.004 | 3 | 8 |

[1]Surface area of region 40 of structure 22 in square inches
[2]% of total filter area that is compressed

Example Three

Figure 3A:
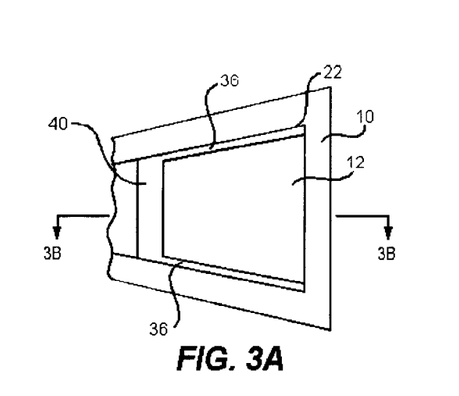
FIG. 3A is a top view of base 10.
Figure 3B:
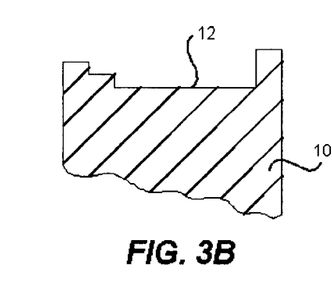
FIG. 3B is a cross-section of base 10 taken along plane 3B—3B in FIG. 3A.
Figure 3C:
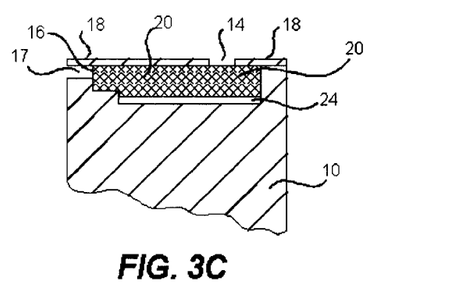
FIG. 3C is a cross section taken along the cross-sectional plane in FIG. 3B of an assembled device including a filter 20, lid 18, and base 10.

FIG. 3 represents an alternative embodiment of a filtration device in accordance with this invention. The embodiment in FIG. 3 is fabricated by conventional methodologies, such as described in Examples 1 and 2. An aspect of this embodiment is the extension of compression structure 22 along two additional sides (lateral compression regions 36) of base 10. Providing lateral compression regions 36 capable of compressing the filter, diminished the possibility that fluid could create a low resistance path along the peripheral surfaces of the filter, whereby particulate matter could contaminate the filtrate. In addition, the lateral compression regions of compression structure 22 provided additional support for the filter 20, minimizing the potential for the filter 20 to touch the bottom of filter cavity 12 in any aspect of dead space 24.

Example Four

FIG. 4 represents an alternative embodiment of a filtration device in accordance with the invention. This embodiment was fabricated in accordance with standard methodologies, such as those described in Examples 1 and 2. An aspect of this embodiment is compression structure 22 which comprises lateral compression regions 36 and proximal compression region 38 so that the perimeter of filter 20 is supported and capable of being compressed. A compression structure 22, as shown in FIG. 4A, is particularly useful when a large bolus of sample is added to the device at a rapid rate. Thus, the extra support given along the edges of the filter will minimize the potential for the filter to touch the bottom of the filter cavity 12 in any aspect of dead space 24.

The embodiment described in this example, and depicted in FIG. 4, provides a larger and more stable compression structure 22 for filter 20. As previously described herein, dead space 24 is beneficial because it has essentially no capillary force, and therefore, dead space 24 remains free of fluid throughout the operation of the embodiment depicted in FIG. 4.

Depending on the manner of sample addition to the filtration device, that is, whether a large bolus of sample is added quickly to the filter, the degree of compression of the filter at the compression region can be increased to about 50% of the filter thickness. This amount of compression, however, impacts the flow rate through the filter. Generally, as the filter is compressed more than about 5% of the filter thickness, the flow rate of the sample moving in the filter is decreased.

Figure 4D:
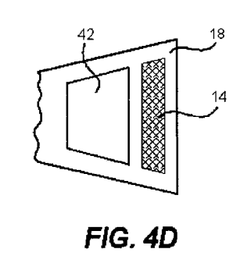
FIG. 4D is a top view of an embodiment comprising a lid cavity 42, depicted in dashed lines.
Figure 4E:
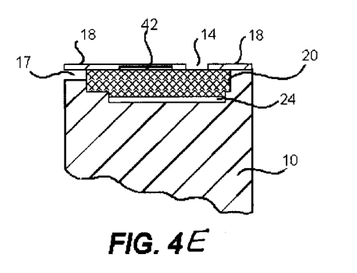
FIG. 4E is a cross section of FIG. 4D taken along the plane 4E—4E.

As illustrated in FIGS. 4D and 4E, lid 18 incorporates a lid cavity 42 which is positioned above filter 20 when lid 18 is assembled to base 10; the lid cavity does not extend into the area above the filter at the compression structure 22. Thus, compression structure 22 is capable of compressing filter 20 to any degree necessary to seal and hold filter 20 in filter cavity 12 without compressing the complete filter 20 against the lid 18, thereby potentially slowing overall fluid flow through filter 20.

Table 2 shows the effect of varying the areas of the proximal 38 and lateral 36 regions, wherein the area of distal compression region 40 was held constant. The results showed that as the total areas were increased from having no lateral or proximal compression region to a combined area of 0.05 in$^2$, the flow rate decreased from 5 $\mu$l/min to 0.5 $\mu$l/min.

Thus, Table 2 provides data showing the impact on flow rate due to variations in the combined area of proximal region 38 and lateral region 36 of compression structure 22.

TABLE 2

EFFECT OF VARIATION OF COMBINED AREAS OF
PROXIMAL REGION 38 AND LATERAL REGION 36,
ON FLUID FLOW RATE
(AREA OF 40 WAS CONSTANT)

| AREA[1] | % AREA COMP[2] | FLOW RATE $\mu$l/MIN |
|---|---|---|
| 0 | 0 | 5 |
| 0.01 | 8 | 2 |
| 0.025 | 20 | 1 |
| 0.05 | 39 | 0.5 |

[1]Combined area of proximal region 38 and lateral regions 36 of structure 22 in square inches
[2]% of total filter area that is compressed

Example Five

Figures 5B, 5C:
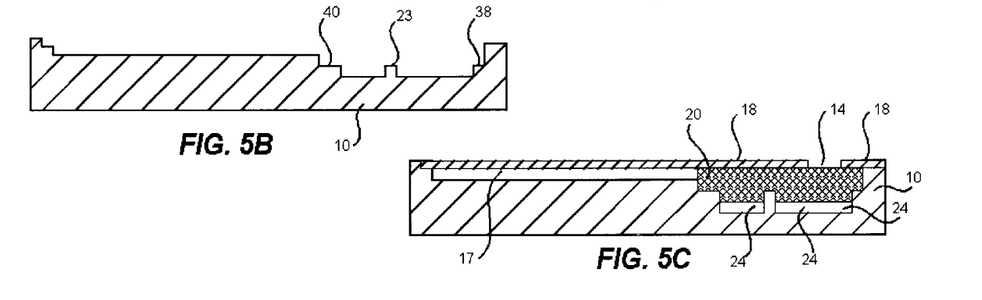
FIG. 5B is a cross-section of base 10 viewed along the plane 5B—5B of FIG. 5A.
FIG. 5C is a cross section, along the same plane as 5B, of an assembled device including a filter 20, lid 18, and base 10.

FIG. 5 illustrates another embodiment of compression structure 22. Specifically, compression structure 22 was extended to comprise support bar 23 (FIGS. 5A, 5B), that divided dead space 24 into two separate dead spaces. Support bar 23 of compression structure 22 added additional support to the filter in the area of the filter 20 which is adjacent and slightly downstream to fluid access port 14. In addition, support bar 23 can provide for a differential compression as compared to other regions of the compression structure 22. Support bar 23 can provide just enough compression on a small surface area of the filter such that flow of sample between a peripheral filter surface and the cavity wall is eliminated, but not so much compression as to impede or cease fluid flow through the device.

Table 3 depicts data for flow rate based on variations in the area of distal compression region 40 of compression structure 22. Table 3 provides empirical data that relates flow rate, plasma recovery volume, and % filter compression for the embodiment shown in FIGS. 5A–C. Thus, Table 3 illustrates that compressing filter 20 from 4% to 31% of the native filter thickness at distal compression region 40, decreased the flow rate from about 3 $\mu$l/min to 2 $\mu$l/min while maintaining region specific compression. The data of Table 3 was taken by adding fresh human whole blood to the inlet port of devices embodied as illustrated in FIG. 5. Each such device consisted of base 10 (Polysar, Polysar Incorporated, Madison, CT, NAS® 30) ultrasonically bonded to lid 18 with filter 20 (Ahlstrom CytoSep, Lot 94-49B, 0.066 cm thick) placed therebetween.

TABLE 3

| Distal Filter Compression (%) | Flow rate of Plasma Exiting Filter (μl/min.) | Plasma Recovery Volume (μl) |
|---|---|---|
| 4 | 3 | 6 |
| 15 | 3 | 6 |
| 23 | 2.5 | 8 |
| 31 | 2 | 8 |

Preferably, the surface area of the compression structure 22 that contacts filter 20 is held to a minimum. If one were to compress the entire filter, the flow rate and filtrate fluid recovery from filter 20 would substantially decrease because the effective porosity of the total filter would be lowered.

In each of Examples 2–5, the sealing of filter 20 comprised use of compression in certain regions of filter 20. With each example, a variation in the shape of compression structure 22 was made. The choice of a compression region configuration for use with a particulate sample is appreciated readily by one of ordinary skill in the art in view of the present disclosure, based on the extent to which one wishes to emphasize parameters such as filter support, flow rate or particle retardation. For example, inclusion of compression structure 22 in FIG. 3 reduced the leakage of red blood cells into the plasma and increased separation efficiency while maximizing flow rate.

Example 6

FIGS. 6A–D illustrates a presently preferred embodiment of the invention. This embodiment provided a sample reservoir 26 (FIG. 6D) which safely contains a fluid sample. Sample reservoir 26 preferably comprises a capillary space, and is in fluid communication with filter 20 and exit region 17.

The embodiment depicted in FIG. 6 was fabricated as follows: base 10 was fabricated using injection molding technology and was made of white acrylic copolymer (Polysar NAS® 30). The overall device length, width and thickness were approximately 8.7, 3.5 and 0.26 cm, respectively. The surface of base 10 was made hydrophilic by treatment with a gas plasma in accordance with standard methodologies, alternatively corona discharge treatment was used to make the surface hydrophilic.

As depicted in FIG. 6D, a slightly oversized filter 20 was fitted over compression structure 22 and a dual region dead space 24. Filter 20 (Ahlstrom CytoSep® filter, Mt. Holly Springs, Pa.) comprised a mixture of cellulose, borosilicate glass, and polyester fibers. Its thickness was 0.063 cm and had an absorption volume of approximately 200 μl. To enhance filter support, filter posts 28 were added, these posts are believed to improve the stability and positioning of filter 20.

Lid 18, formed of clear plastic, was ultrasonically welded to base 10. The lid had dimensions of approximately 8, 2.5 and 0.1 cm. Bonding lid 18 to base 10 resulted in a slight compression of filter 20 of approximately 4% relative to its native thickness. Region-specific compression at structure 22 created a seal that helped to prevent fluid and particle flow over peripheral surfaces of filter 20.

Tables 4–6 contain flow rate data for exit region 17. The data for Tables 4–6 were obtained from experiments wherein at least 15 μl of filtrate fluid was obtained.

For example, as indicated in Table 4, a 25% compression of filter 20 by compression structure 22 slowed the flow rate of the sample by as much as 23% in the filter. Increasing the compression to about 50% decreased the flow rate by up to 61%.

TABLE 4

EFFECT ON FLUID FLOW BY FILTER COMPRESSION (THICKNESS) BY DISTAL COMPRESSION REGION 40 OF COMPRESSION STRUCTURE 22

| % Compression | Flow Rate μl/min | % decrease in fluid flow |
|---|---|---|
| 1 | 6.4 | Control |
| 25 | 4.9 | 23% |
| 50 | 2.5 | 61% |

Table 5 shows the effect of filter compression by support bar 23 on the fluid flow from the filter. A constant 1% compression of filter 20 at the distal compression region 40 was the control. As the compression of the filter thickness by support bar 23 increased from 1% to 50%, the flow rate dropped from 6.4 μl/min to 1.7 μl/min.

TABLE 5

EFFECT ON FLUID FLOW BY FILTER COMPRESSION (THICKNESS) BY SUPPORT BAR 23

| % Compression | Flow Rate μl/min | % decrease in fluid flow |
|---|---|---|
| 1 | 6.4 | Control |
| 25 | 3.0 | 53% |
| 50 | 1.7 | 73% |

Table 6 shows the effect of filter compression at both distal region 40 and support bar 23, on fluid flow rate from the filter. As the compression regions increased filter compression from 1% to 50%, the flow rate decreased from 6.4 μl/min to 1.8 μl/min.

TABLE 6

EFFECT ON FLUID FLOW BY FILTER COMPRESSION (THICKNESS) BY DISTAL REGION 40 AND SUPPORT BAR 23

| % Compression | Flow Rate μl/min | % decrease in fluid flow |
|---|---|---|
| 1 | 6.4 | Control |
| 25 | 2.9 | 55% |
| 50 | 1.8 | 72% |

The sample flow rate decreased since pores or matrices of the filter are made smaller by compression and the resistance to flow is increased. As disclosed herein, compression of the filter at compression structure 22 can be as great as 50% if lid 18 has been modified to comprise lid cavity 42, as shown in FIG. 4D, without a substantial decrease in fluid flow rate.

Fluid access port 14 was located over sample reservoir 26. One skilled in the art will recognize that the fluid access port 14 can be situated over the sample reservoir 26, as well as a portion of filter 20 (FIG. 6D). Lid 18 and base 10 formed a fluid exit region 17 (FIG. 6D) adjacent to the downstream edge of filter 20 (i.e., adjacent fluid egress region 16 of filter 20). The fluid exit region preferably can comprise a capillary space. In an embodiment where exit region 17 comprised a capillary, exit region 17 had cross-sectional dimensions adjacent filter egress region 16 of 25 μm by 1.0 cm to create a capillary gap (also referred to herein as a capillary space). The dimension of a fluid egress region comprising a capillary can vary from about 0.1 μm to about 100 μm, and most preferably from about 10 μm to 50 μm.

The capillarity of exit region 17 was important for embodiments where fluid was drawn into the exit region without an external applied pressure at any point before or along the flow path. For such embodiments, the relative capillarity of filter 20 and the exit region 17 were designed to provide fluid movement from the filter into the exit capillary. Thus, exit region 17 will have the highest capillarity, filter 20 will have intermediate capillarity and sample reservoir 26 will have lowest capillarity. The capillarity of the sample reservoir should not be so great as to prevent fluid from entering the filter and the downstream capillaries of the device, particularly devices as described in U.S. Patent No. 5,458,852.

As depicted in FIG. 6D, sample reservoir 26, is in fluid communication with the top, bottom and edge of filter 20. One skilled in the art will recognize that the surface area of the filter in contact with fluid in sample reservoir 26 can be varied, and that maximizing the surface area of the filter in contact with fluid will improve the filtration characteristics of the filter because particulate matter incapable of penetrating the filter is spread out over a larger area, whereby the filter will have a lower tendency to clog.

Sample reservoir 26 also facilitates addition of various volumes of sample to the device. One skilled in the art will recognize that the volume of the sample reservoir 26 should be adjusted to accommodate the volume of sample to be assayed by the device. Preferred volumes for the sample reservoir are between 0.1 μl and 1000 μl, and particularly preferred volumes are between 5 μl and 300 μl.

In one embodiment, sample reservoir 26 comprises a capillary space when a lid 18 is attached to the base 10; therefore, the dimensions of the capillary gap of the reservoir 26 are designed in accordance with the capillarity of the regions of the entire device, so that there will be fluid flow and filtration.

Advantageously, the capillary force of the fluid reservoir 26 held the fluid sample within the reservoir and minimized the risk of spilling or expulsion of fluid sample from the device. This is particularly advantageous when the fluid sample is, e.g., a biological fluid that may be contaminated with hazardous bacteria or virus, or is an environmental water sample contaminated with pollutants.

Preferably, reservoir 26 comprises vent holes 30 in lid 18. Vent holes 30 allow escape of air from reservoir 28 during filling with the fluid sample, and facilitate more complete filling of the reservoir.

A particularly preferred embodiment of the sample reservoir 26, as illustrated in FIG. 6, comprises grooves 34 on the floor of reservoir 26 and on the filter stay 32. In the absence of grooves (or other suitable texture), when the floor of the sample reservoir 26 was flat, some sample fluid was retained by capillary action in the corners of the sample reservoir 26. In one embodiment, grooves 34 are approximately 0.013 cm deep and 0.043 cm wide and are oriented such that the sample fluid is directed to filter 20 by flowing along grooves 34. Thus, the sample fluid completely drained from the corners of the sample reservoir 26, since grooves 34 served to break the capillary tension of the sample fluid meniscus that formed in the corners of sample reservoir 26 that occurred as sample fluid was depleted from the reservoir.

One skilled in the art will recognize that the size and orientation of the grooves can be changed and the grooves could be substituted for a surface texture of posts protruding from the floor of the sample reservoir without changing the scope of this invention.

In the particular embodiment with dimensions discussed in this example, fresh human whole blood (220 μl), drawn in a Vacutainer® Blood Collection Tube with EDTA, was added through fluid access port 14, into sample reservoir 26; the fluid simultaneously began to flow into filter 20. Blood continued to move from sample reservoir 26 into filter 20 because filter 20 had a stronger capillary force than sample reservoir 26. The fluid flowed laterally through filter 20, and two distinct flow fronts developed, the leading front being clear plasma and the trailing front comprising particulate material such as red blood cells. The plasma front reached the downstream edge of filter 20 (i.e., fluid egress region 16) after about 50 seconds at which point the plasma front was approximately 2 mm ahead of the red blood cell front. Within filter 20 having dimensions disclosed above, the volume of plasma that a 2 mm distance corresponded to was approximately 20 to 30 μl. This volume represented the amount of plasma available for an assay before the red blood cells reached the downstream edge of filter 20 and could move into exit region 17; this configuration was selected because a volume of 15 to 20 μl was necessary to obtain an assay result. Fluid flow through filter 20 was enhanced by the capillary force of exit region 17. As noted above, exit region 17 comprised a capillary space, and plasma exited the filter and entered exit region 17 by capillary action, at a flow rate of approximately 7 μl/min. Approximately 15 to 20 μl of plasma was recovered and was devoid of red blood cells.

In a preferred embodiment, to minimize the possibility that a filtrate fluid in exit region 17 might be contaminated with particulate matter, the exit region was designed to accommodate a volume which corresponded to the volume of fluid that was equal to or less than that which precedes the particulate matter front for a given device embodiment. Thus, in the embodiment depicted in FIG. 6, with dimensions as set forth above, the exit region was designed to accommodate 20–30 μl or less.

What is claimed is:

1. A device comprising:
    a housing comprising a lid, a base substantially parallel to the lid, and a fluid access port in the lid;
    a fluid permeable filter within the housing comprising a region for fluid access fluidly connected to the fluid access port, and a region for fluid egress, wherein the filter comprises a substantially smaller depth dimension in comparison to its length and width dimensions, wherein the length/width plane of the filter is oriented within the housing substantially parallel to the lid and base, and wherein said filter is compressed in one specific region, but not in all regions of said filter, whereby fluid and particulate matter flow in said compressed region is retarded;
    a fluid flow path through the filter that is a lateral flow path from the region for fluid access through the filter to the region for fluid egress; and
    a fluid egress port in the base or between the lid and base comprising a capillary space fluidly connected to the region of fluid egress from the filter, wherein fluid flows from said filter to said capillary space.

2. The device of claim 1, wherein one or more peripheral surfaces of the filter are sealed in a fluid tight manner.

3. The device of claim 1, further comprising a dead space defined by a peripheral surface of the filter and a region of the device.

4. The device of claim 1, wherein said at least one compressed region of the filter is compressed using fluid-impermeable glue, a sealant, or a pressure adhesive tape.

5. The device of claim 1, wherein said at least one compressed region of the filter is compressed between two or more solid surfaces.

6. The device of claim 1 wherein the capillary space fluidly connected to the fluid egress region comprises a means for producing an assay result.

7. The device of claim 1 further comprising a sample reservoir fluidly connected to the fluid access region of the filter.

8. The device of claim 7 wherein the sample reservoir comprises a capillary space.

9. A method for assaying fluid samples, the method comprising adding fluid to the fluid access port of the device of claim 7.

10. The device of claim 1, wherein movement of any particulate matter in the filter through a peripheral surface of the filter is retarded.

11. The device of claim 10, wherein the filter is sealed in a particle-tight manner on all peripheral surfaces, whereby for a sample comprising particulate matter, any particulate matter in the filter is retained in the filter and any fluid in a capillary space along a peripheral surface of the filter is free of particulate matter.

12. The device of claim 11, wherein the filter is sealed in a liquid-tight manner on all peripheral surfaces.

13. The device of claim 11, wherein the filter is sealed in a fluid-tight manner on all peripheral surfaces.

14. A device comprising:
   a housing comprising a lid, a base substantially parallel to the lid, and a fluid access port within the lid;
   a filter within the housing capable of separating particulate matter from liquid matter in a fluid sample, said filter comprising a fluid access region fluidly connected to the fluid access port and a fluid egress region, wherein the filter is compressed in one specific region, but not in all regions of said filter, whereby fluid and particulate matter flow in said compressed region is retarded;
   a fluid egress port within the base or between the lid and base fluidly connected to the region of fluid egress from the filter; and
   a fluid flow path through the filter that is in a lateral path from the fluid access region through the filter to the fluid egress region, wherein fluid flows from said filter to said fluid egress port.

15. The device of claim 14, wherein the lateral flow path has a distance greater than or equal to a transverse flow path distance through the filter.

16. The device of claim 14, wherein particulate matter in a fluid sample is retarded from moving from the filter and into a capillary space external to the filter and adjacent to a peripheral filter surface through the use of a fluid-impermeable glue, a sealant, or a pressure adhesive tape.

17. The device of claim 14, wherein said at least one compressed region of the filter is compressed between two or more solid surfaces.

18. The device of claim 14, wherein said at least one compressed region of the filter is compressed by about 1–50% of the native thickness of the filter.

* * * * *